United States Patent
Sun et al.

(10) Patent No.: US 9,144,497 B2
(45) Date of Patent: Sep. 29, 2015

(54) ACETABULAR CUP FOR AN ARTIFICIAL HIP JOINT AND BEARING, AND ACETABULAR CUP ASSEMBLY

(75) Inventors: Doo Hoon Sun, Seoul (KR); Yong Sik Kim, Seoul (KR); Kyung Hoi Koo, Gyeonggi-do (KR); Yong-Chan Ha, Gyeonggi-do (KR); Young-Kyun Lee, Seoul (KR)

(73) Assignee: CORENTEC CO., LTD., Chungcheongnam-do (KR)

( * ) Notice: Subject to any disclaimer, the term of this patent is extended or adjusted under 35 U.S.C. 154(b) by 139 days.

(21) Appl. No.: 13/982,168

(22) PCT Filed: Nov. 9, 2011

(86) PCT No.: PCT/KR2011/008506
§ 371 (c)(1),
(2), (4) Date: Jul. 26, 2013

(87) PCT Pub. No.: WO2012/108610
PCT Pub. Date: Aug. 16, 2012

(65) Prior Publication Data
US 2013/0310946 A1   Nov. 21, 2013

(30) Foreign Application Priority Data
Feb. 9, 2011   (KR) .................. 10-2011-0011459

(51) Int. Cl.
*A61F 2/32*   (2006.01)
*A61F 2/34*   (2006.01)
*A61F 2/30*   (2006.01)

(52) U.S. Cl.
CPC ......... *A61F 2/34* (2013.01); *A61F 2002/30331* (2013.01); *A61F 2002/30367* (2013.01); *A61F 2002/30607* (2013.01); *A61F 2002/3401* (2013.01); *A61F 2002/3403* (2013.01); *A61F 2002/3411* (2013.01)

(58) Field of Classification Search
CPC .............. A61F 2/32; A61F 2220/0033; A61F 2002/3241; A61F 2/34
USPC ............................................. 623/22.11–22.39
See application file for complete search history.

(56) References Cited

U.S. PATENT DOCUMENTS 4,180,873 A * 1/1980 Fixel .......................... 623/22.23
5,314,487 A * 5/1994 Schryver et al. ........... 623/22.37
(Continued)

FOREIGN PATENT DOCUMENTS

KR   2005-0100511 A   10/2005

OTHER PUBLICATIONS

International Search Report and Written Opinion dated Jun. 26, 2012, issued in PCT application No. PCT/KR2011/008506.

*Primary Examiner* — Jason-Dennis Stewart
(74) *Attorney, Agent, or Firm* — Workman Nydegger (57) ABSTRACT

An acetabular cup assembly for an artificial hip joint includes an acetabular cup including a seating recess, a female taper formed on an inner wall, protrusion recesses formed to communicate with the seating recess and insertion recesses each positioned inside a corresponding one of the protrusion recesses; and a bearing including a male taper on an outer circumference thereof, protrusions inserted into the protrusion recesses, and insertion protruding portions each formed on a corresponding one of the protrusions, the insertion protruding portions being inserted into the insertion recesses. A polyethylene bearing can be firmly fixed to the acetabular cup. When a ceramic bearing made is inserted into the acetabular cup, the area where the bearing adjoins the acetabular cup is increased, thereby preventing the ceramic bearing from being broken. Since no groove is formed along the entire circumference of the acetabular cup, the strength is increased.

8 Claims, 6 Drawing Sheets

(56) References Cited

U.S. PATENT DOCUMENTS

| | | |
|---|---|---|
| 6,475,243 B1 * | 11/2002 | Sheldon et al. ............ 623/22.28 |
| 6,610,097 B2 | 8/2003 | Serbousek et al. |
| 7,169,186 B2 | 1/2007 | Harris et al. |
| 2004/0204767 A1 | 10/2004 | Park et al. |
| 2008/0114459 A1 * | 5/2008 | Scott et al. ................ 623/18.11 |
| 2009/0088866 A1 * | 4/2009 | Case .......................... 623/22.21 |
| 2010/0185297 A1 | 7/2010 | Steinberg |
| 2011/0015753 A1 | 1/2011 | Meridew |

\* cited by examiner

ACETABULAR CUP FOR AN ARTIFICIAL HIP JOINT AND BEARING, AND ACETABULAR CUP ASSEMBLY

TECHNICAL FIELD

The present invention relates to an acetabular cup assembly for an artificial hip joint, and more particularly, to an acetabular cup assembly for an artificial hip joint which includes an acetabular cup and a bearing which is seated in the seating recess, in which the acetabular cup has a seating recess, a female taper formed on an inner wall, protrusion recesses formed to communicate with the seating recess and insertion recesses each positioned inside a corresponding protrusion recess, and the bearing has a male taper on an outer circumference thereof, protrusions which are inserted into the protrusion recesses, and insertion protruding portions each formed on a corresponding one of the protrusions, the insertion protruding portions being inserted into the insertion recesses.

BACKGROUND ART

The hip joint is the joint that connects between the thighbone and the hipbone of the pelvis in the body. The hip joint performs the most important function when a person sits or stands. The hip joint can be damaged by a pathological reason such as tuberculosis, an external wound, or the like. In order to cure the damaged hip joint, an artificial implant for a hip joint can be implemented by a surgical operation. Typically, an artificial implant for a hip joint includes a stem and an acetabular cup. The stem and the acetabular cup are fabricated from, for example, a body-friendly material such as a Ti alloy. The stem for the artificial hip joint is inserted into and fixed to the thighbone, and the acetabular cup is fixed to the acetabulum of the pelvis. A globe made of a ceramic or metal material is fixed to one end of the stem, and a bearing having a corresponding shape is inserted into the cup, such that the globe can be received and rotate in the bearing. The bearing has a concave hemispherical inner surface such that the globe fixed to the one end of the stem can rotate therein, thereby enabling the joint motion. The bearing is also made of a ceramic or polymer polyethylene material.

An approach for allowing bearings made of different materials to be selectively inserted into one acetabular cup for use is disclosed in U.S. Pat. No. 6,610,097.

In order for the ceramic bearing to be inserted into the acetabular cup, a taper portion is formed on the inner portion of the acetabular cup and on the outer circumference of the bearing.

In addition, in order for the polyethylene bearing to be inserted, several recesses are formed in the lower end of the acetabular cup, and a circular recess is formed along the inner circumference so as to be positioned above the recesses. In addition, several locking portions which are inserted into the recesses are formed along the circumference, and circular fixing portions are positioned above the locking portions such that the fixing portions are inserted into the circular recess.

However, when the ceramic bearing is inserted into the acetabular cup via the circular recess, the area in which the bearing adjoins the acetabular cup is reduced by the cross-sectional area of the circular recess. Therefore, the ceramic bearing can be easily broken, which is problematic.

In addition, the circular recess also causes the overall strength of the acetabular cup to be decreased, which is problematic.

RELATED ART DOCUMENT

Patent Document 1: U.S. Pat. No. 6,610,097

DISCLOSURE

Technical Problem

Accordingly, the present invention has been made keeping in mind the above problems occurring in the prior art, and an object of the present invention is to provide an acetabular cup assembly for an artificial hip joint, in which a bearing made of polyethylene can be firmly fixed to an acetabular cup, and when a bearing made of ceramic is inserted into the acetabular cup, the area in which the bearing and the acetabular cup adjoin each other is increased, thereby preventing the ceramic bearing from being broken. In addition, since no groove is formed along the entire circumference of the acetabular cup, the strength is increased.

Technical Solution

In order to accomplish the above object, the present invention provides an acetabular cup assembly for an artificial hip joint that includes: an acetabular cup comprising a seating recess, a female taper formed on an inner wall, protrusion recesses formed to communicate with the seating recess and insertion recesses each positioned inside a corresponding one of the protrusion recesses; and a bearing comprising a male taper on an outer circumference thereof, protrusions inserted into the protrusion recesses, and insertion protruding portions each formed on a corresponding one of the protrusions, the insertion protruding portions being inserted into the insertion recesses.

The insertion recess may be inclined so as to become thicker in a direction toward bottom. The bearing may have first recesses in the outer circumference thereof, the first recesses being positioned at side portions of the protrusions. The bearing may have second recesses along the outer circumference thereof, the second recesses being positioned at upper portions of the protrusions.

In order to accomplish the above object, the present invention also provides an acetabular cup for an artificial hip joint that includes a seating recess, a female taper formed on an inner wall, protrusion recesses formed in a radial direction, the protrusion recesses communicating with the seating recess, and insertion recesses formed in a top-bottom direction, each of the insertion recesses being positioned inside a corresponding one of the protrusion recesses.

In order to accomplish the above object, the present invention also provides a bearing for an artificial hip joint that includes a male taper on an outer circumference thereof, protrusions formed in radial direction on the outer circumference and insertion protruding portions each formed in a corresponding one of the protrusions, the insertion protruding portions extending in a top-bottom direction.

Advantageous Effects

The acetabular cup, bearing and acetabular cup assembly for an artificial hip joint according to the present invention as described above have the following effects.

The acetabular cup has the seating recess, the female taper formed on the inner wall, the protrusion recesses communicating with the seating recess and the insertion recesses which are positioned inside the protrusion recesses. The bearing has the male taper on the outer circumference thereof, the protrusions each formed on a corresponding protrusion, the insertion protruding portions being inserted into the insertion recesses. Therefore, the bearing made of polyethylene can be firmly fixed to the acetabular cup, and when the ceramic bearing is inserted into the acetabular cup, the area in which the bearing and the acetabular cup adjoin each other is increased, thereby preventing the ceramic bearing from being broken. In addition, since no groove is formed along the entire circumference of the acetabular cup, the strength is increased.

Since each of the insertion protruding portions is formed such that it becomes thicker in the direction toward bottom, the bearing can be easily inserted into the acetabular cup.

The first recesses are formed in the outer circumference of the bearing so as to be positioned at side portions of the protrusions, thereby preventing the bearing from interfering with protrusions which are formed when machining the protrusion recesses in the acetabular cup.

The second recesses are formed in the outer circumference of the bearing such that they are positioned at upper portions of the protrusions. This advantageously reduces buffs that are produced when machining the bearing.

MODE FOR INVENTION

Reference will now be made in detail to various embodiments of the present invention, which are illustrated in the accompanying drawings.

For reference, descriptions of some features of the present invention will be omitted hereinafter when they are identical to those of the related art and descriptions of those of the related art will be referred to.

As shown in FIG. 1 to FIG. 6, the acetabular cup assembly for an artificial hip joint according to this embodiment includes an acetabular cup 100 and a bearing 200. The acetabular cup 100 has a seating recess 140, a female taper 101 on the inner wall, protrusion recesses 150 communicating with the seating recess 140, and fitting recesses 151 which are disposed inside the protrusion recesses 150. The bearing 200 is seated in the seating recess 140, has a male taper 201 on the outer circumference thereof and protrusions 250 which are fitted into the protrusion recesses 150. Each of the protrusions 250 has a fitting protruding portion 251 which is fitted into the fitting recess 151.

Figure 1:
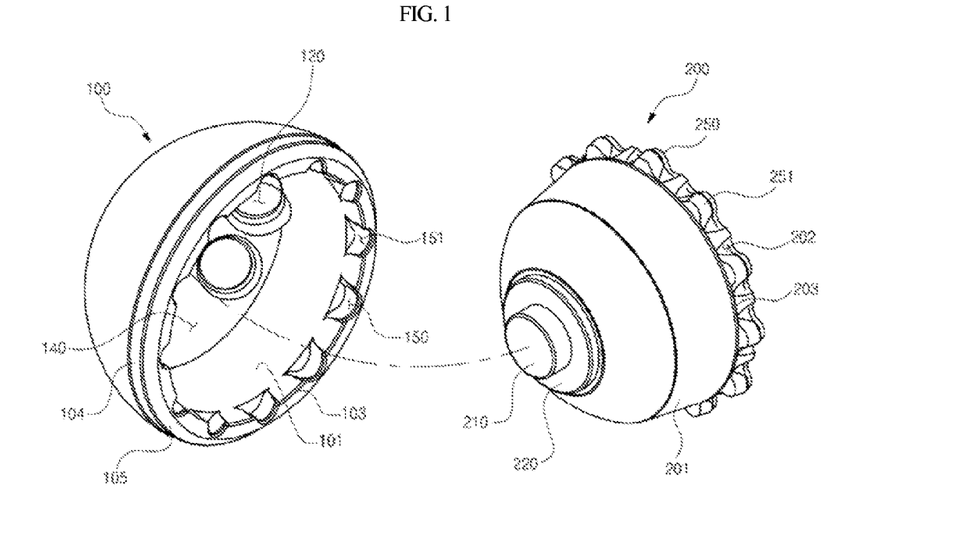
FIG. 1 is an exploded perspective view showing an acetabular cup assembly for an artificial hip joint according to an exemplary embodiment of the invention.
Figure 4:
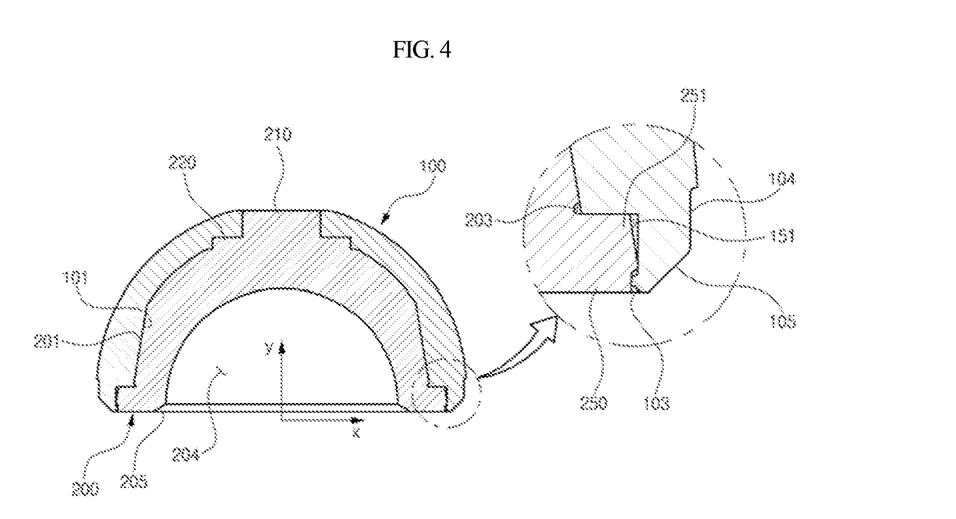
FIG. 4 is an assembled cross-sectional view of the acetabular cup assembly for an artificial hip joint shown in FIG. 1.
Figure 5:
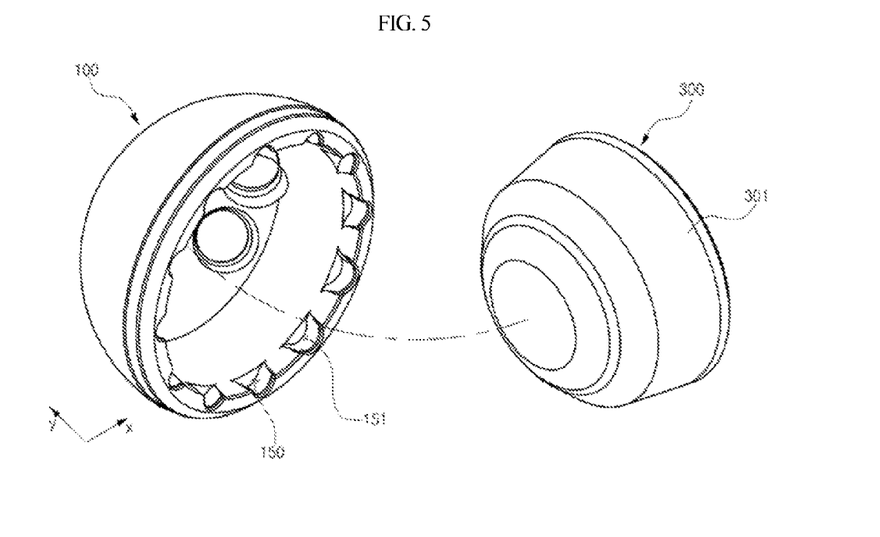
FIG. 5 is an exploded perspective view of an acetabular cup assembly for an artificial hip joint according to an exemplary embodiment of the invention.

As shown in FIG. 1 and FIG. 4, the acetabular cup 100 is substantially hemispherical, and the seating recess 140 having an arc shape is formed in the lower portion of the acetabular cup 100.

Figure 2:
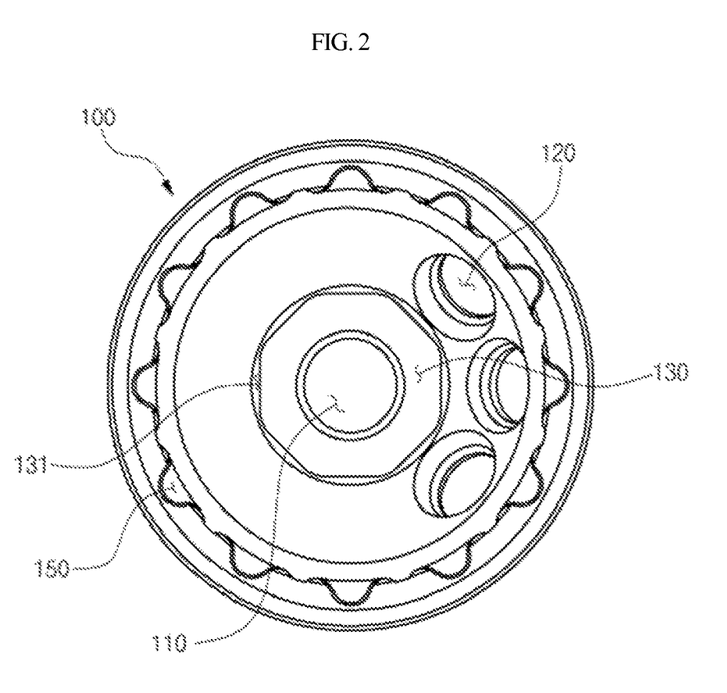
FIG. 2 is a bottom view of the acetabular cup for an artificial hip joint shown in FIG. 1.

As shown in FIG. 2, an insertion hole 110 is formed in and perforates the central portion of the acetabular cup 100 such that it communicates with the seating recess 140.

A polygonal surgical instrument recess 130 is formed in the inner wall of the acetabular cup 100 such that it communicates with the insertion hole 110.

In addition, an auxiliary seating recess 131 is formed in the inner wall of the acetabular cup 100 such that it surrounds the surgical instrument recess 130.

The acetabular cup 100 has screw fastening holes 120 into each of which a screw (not shown) is fitted, the screw fastening holes 120 being located at the side of the insertion hole 110.

There are three screw fastening holes 120, and they are oriented at 40 degrees from each other.

The female taper 101 is formed along the entire area of the inner wall of the acetabular cup 100 such that it is disposed below the screw fastening holes 120.

Figure 3:
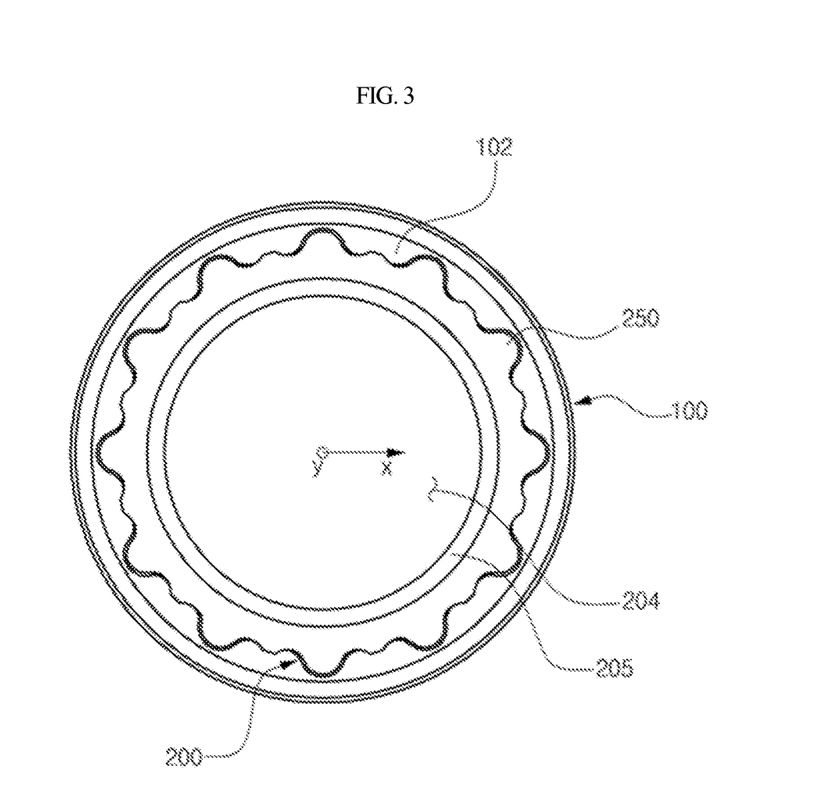
FIG. 3 is an assembled bottom view of the acetabular cup assembly for an artificial hip joint shown in FIG. 1.

As shown in FIG. 3, the acetabular cup 100 has the protrusion recesses 150 which are disposed in the radial direction x such that they communicate with the seating recess 140.

The protrusion recesses 150 are formed in a plural number (e.g. 12), and the plurality of protrusion recesses 150 are disposed along the circumferential direction of the protrusion recess 150.

The protrusion recesses 150 are formed in the bottom of the inner wall of the acetabular cup 100.

The acetabular cup 100 has the insertion recesses 151 which are formed in the top-bottom direction y and are disposed inside the protrusion recesses 150.

The insertion recesses 151 are disposed in the upper portion of the protrusion recesses 150.

An inclined surface 103 is formed on the lower end of the inner wall of the acetabular cup 100 such that it is positioned on the lower portion of the protrusion recess 150. This inclined surface 103 facilitates the assembly between the acetabular cup 100 and the bearing 200 which will be described later, since the bearing 200 can slide along the inclined surface 103.

A stepped portion 104 is formed along the entire outer circumference of the lower portion of the acetabular cup 100.

An outer inclined surface 105 is formed on the outer circumference of the acetabular cup 100 at a position below the stepped portion 104.

The bearing 200 is hemispherical, and is seated in the seating recess 140.

The bearing 200 is made of a polyethylene material.

In the lower portion of the bearing 200, a hemispherical head seating recess 204 is formed. A head (not shown, formed in a stem) is inserted into the head seating recess 204.

A chamber 205 is formed in the lower end of the inner wall of the bearing 200.

The chamber 205 prevents the head and the bearing 200 from interfering with each other, thereby increasing the range in which the head moves.

A first insertion protrusion 210 which is inserted into the insertion hole 110 is formed in the upper central portion of the bearing 200. The first insertion protrusion 210 prevents the bearing 200 from tilting with respect to the acetabular cup 100 after the assembly.

The bearing 200 has a second insertion protrusion 220 which surrounds the first insertion protrusion 210 and is seated in the auxiliary seating recess 131.

The male taper 201 is formed on the outer circumference of the bearing 200, the male taper 201 corresponding to the female taper 101.

The outer diameter of the male taper 201 is slightly greater than the inner diameter of the female taper 101.

The male taper 201 and the female taper 101 prevent the bearing 200 which is assembled to the acetabular cup 100 from minutely moving (micro-motion) with respect to the acetabular cup 100.

The protrusions 250 are formed on the lower end of the outer circumference of the bearing 200 in the radial direction x.

The protrusions 250 of the bearing 200 are inserted into the protrusion recesses 150 of the acetabular cup 100.

The protrusions 250 have an arc-shaped horizontal cross-section, and a fitting protruding portion 251 is formed on the outer portion of each of the protrusions 250 in the top-bottom direction y.

The insertion protruding portions 251 of the bearing 200 are inserted into the insertion recesses 151 of the acetabular cup 100, each insertion protruding portions 251 being shaped such that it becomes thicker in the direction toward bottom. Therefore, the outer surface of each insertion protrusions 251 is inclined.

The bearing 200 is easily inserted into the acetabular cup 100 since the inclined outer surfaces of the insertion protruding portions 251 slide on the acetabular cup 100.

Since the bearing 200 is made of a polyethylene material, the insertion protruding portions 251 can be elastically deformed. Consequently, the insertion protruding portions 251 are shrunk when the bearing 200 is being assembled to the acetabular cup 100. Upon completion of the assembly, insertion protruding portions 251 restore the original shape. That is, bearing 200 is assembled to the acetabular cup 100.

First recesses 202 are formed in the outer circumference of the bearing 200 such that they are positioned at side portions of the protrusions 250.

It is preferred that the first recesses 202 be formed on both sides of the protrusions 250.

The first recesses 202 prevent the bearing 200 from interfering with the protrusions 102 which are formed when machining the protrusion recesses 150 in the acetabular cup 100.

Second recesses 203 are formed in the outer circumference of the bearing 202 such that they are positioned at upper portions of the protrusions 250.

The second recesses 203 serve to reduce burrs that are produced when machining the bearing 200.

As an alternative, the bearing 300 can be made of a ceramic material.

Figure 6:
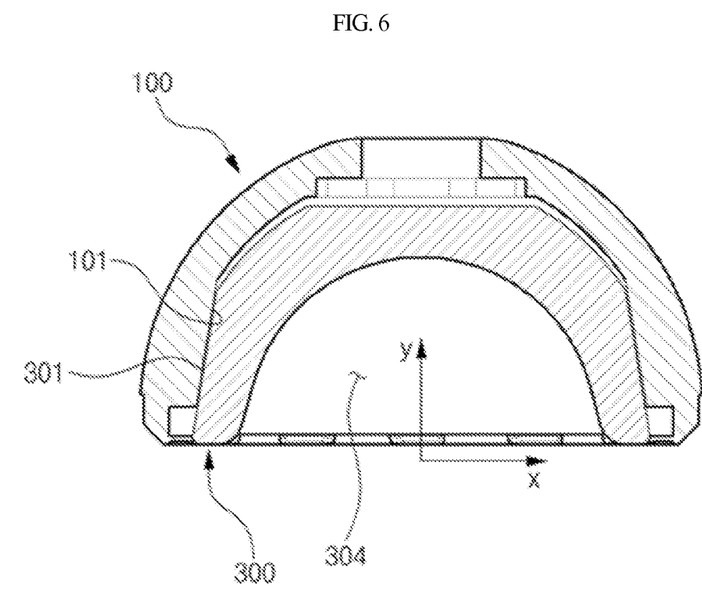
FIG. 6 is an assembled cross-sectional view of the acetabular cup assembly for an artificial hip joint shown in FIG. 5.

As shown in FIG. 6, the ceramic bearing 300 has a head seating recess 304 in the lower portion. The ceramic bearing 300 is hemispherical.

A male taper 301 is formed on the lower portion of the bearing 300, the male taper 301 corresponding to the female taper 101 of the acetabular cup 100.

The female taper 101 and the male taper 301 prevent the bearing 300 from being dislodged from the acetabular cup 100.

Reference will now be made to the process of assembling the acetabular cup 100 and the bearing 200/300 according to embodiments of the invention which have the above-described configuration.

When the polyethylene bearing 200 is inserted into the seating recess 140 of the acetabular cup 100, the female taper 101 and the male taper 201 serve as guides which set the direction of the assembly. In sequence, the insertion protruding portions 251 slide along the inclined surface 103 of the acetabular cup 100 while shrinking, and then return while being inserted into the insertion recess 151. At that moment, the protrusion 250 is inserted into the protrusion recess 150.

Due to the female taper 101, the male taper 201, the first insertion protrusion 210 and the insertion hole 110 as described above, the assembling process can be carried out easily and accurately.

Since the protrusion 250 is inserted into the protrusion recess 150 as such, the bearing 200 does not rotate with respect to the acetabular cup 100.

In addition, since the insertion protruding portions 251 are inserted into the insertion recesses 151, the bearing 200 is not dislodged from the acetabular cup 100.

In addition, as shown in FIG. 6, when the ceramic bearing 200 is inserted into the seating recess 140 of the acetabular cup 100, only the female taper 101 and the male taper 301 adjoin each other. This accordingly prevents the bearing 300 from being dislodged from the acetabular cup 100.

As set forth above, the present invention can firmly fix the polyethylene bearing 200 to the acetabular cup 100. In addition, in some circumstances, when the ceramic bearing 300 is inserted into the acetabular cup 100, the area in which the bearing 300 the acetabular cup 100 adjoin each other is increased more than the area in which a bearing and an acetabular cup of the related art adjoin each other. This consequently prevents the ceramic bearing 300 from being broken. In addition, since no groove is required along the entire circumference of the inner wall of the acetabular cup 100 in order to prevent the polyethylene bearing 200 from being dislodged, the strength of the acetabular cup 100 is improved.

In addition, the invention is applicable not only to the artificial hip joint but also to the other artificial joints of the body.

Although the preferred embodiments of the present invention have been disclosed for illustrative purposes, those skilled in the art will appreciate that various modifications or variations are possible without departing from the scope and spirit of the invention as disclosed in the accompanying claims.

| Description of the Reference Numerals in the Drawings | |
| --- | --- |
| 100: acetabular cup | 101: female taper |
| 102: protrusion | 110: insertion hole |
| 120: screw fastening hole | |
| 130: surgical instrument recess | |
| 140: seating recess | 150: protrusion recesses |
| 151: fitting recesses | 200, 300: bearing |
| 201, 301: male taper | |
| 210: first insertion protrusion | |
| 220: second insertion protrusion | |
| 202: first recess | 203: second recess |
| 204, 304: head seating recess | |
| 250: protrusion | |
| 251: insertion protruding portion | |

The invention claimed is:

1. An acetabular cup assembly for an artificial hip joint, comprising:

an acetabular cup comprising a seating recess surrounded and defined by an inner wall where a female taper is formed along an entire area, a plurality of protrusion recesses formed in the bottom of the inner wall and caved in a predetermined depth in the radial direction such that they communicate with the seating recess and are disposed along a circumferential direction, and a plurality of insertion recesses formed inside the plurality of protrusion recesses and caved in a predetermined depth; and a bearing comprising a polyethylene bearing made of a polyethylene material which comprises an outer circumference having a male taper, a plurality of protrusions protruding in the radial direction on the lower portion of the outer circumference, and a plurality of insertion protruding portions protruding on the outer portion of each of the protrusions, wherein the plurality of protrusion recesses are disposed along the circumferential direction of the acetabular cup, and the plurality of protrusions are disposed along the circumferential direction of the polyethylene bearing, and in a case where the polyethylene bearing is engaged with the acetabular cup, each protrusion of the polyethylene bearing is inserted into each protrusion recess of the acetabular cup, and each insertion protruding portion of the polyethylene bearing is inserted into each insertion recess of the acetabular cup, and the male taper of the polyethylene bearing is engaged with the female taper of the acetabular cup.

2. The acetabular cup assembly according to claim 1, wherein the insertion protruding portions are inclined so as to become thicker in a direction toward a bottom.

3. The acetabular cup assembly according to claim 1, wherein the polyethylene bearing has a plurality of first recesses in the outer circumference thereof, the plurality of first recesses being positioned at side portions of the protrusions.

4. The acetabular cup assembly according to claim 1, wherein the polyethylene bearing has a plurality of second recesses along the outer circumference thereof, the plurality of the second recesses being positioned at upper portions of the protrusions.

5. An acetabular cup assembly kit for an artificial hip joint, the kit comprising:
an acetabular cup comprising:
a seating recess surrounded and defined by an inner wall where a female taper is formed along an entire area,
a plurality of protrusion recesses formed in the bottom of the inner wall and caved in a predetermined depth in the radial direction such that they communicate with the seating recess and are disposed along a circumferential direction, and
a plurality of insertion recesses formed inside the plurality of protrusion recesses and caved in a predetermined depth; and
a polyethylene bearing made of a polyethylene material which comprises an outer circumference having a male taper, a plurality of protrusions protruding in the radial direction on the lower portion of the outer circumference, and a plurality of insertion protruding portions protruding on the outer portion of each of the protrusions, and
a ceramic bearing made of a ceramic material which comprises an outer circumference having a male taper;
wherein the plurality of protrusion recesses are disposed along the circumferential direction of the acetabular cup, and the plurality of protrusions are disposed along the circumferential direction of the polyethylene bearing, and in case of the polyethylene bearing being engaged with the acetabular cup, each protrusion of the polyethylene bearing is inserted into each protrusion recess of the acetabular cup, and each insertion protruding portion of the polyethylene bearing is inserted into each insertion recess of the acetabular cup, and the male taper of the polyethylene bearing is engaged with the female taper of the acetabular cup,
wherein in a case where the ceramic bearing is engaged with the acetabular cup, the male taper of the ceramic bearing is engaged with the female taper of the acetabular cup.

6. The acetabular cup assembly kit according to claim 5, wherein the insertion protruding portions are inclined so as to become thicker in a direction toward a bottom.

7. The acetabular cup assembly kit according to claim 5, wherein the polyethylene bearing has a plurality of first recesses in the outer circumference thereof, the plurality of first recesses being positioned at side portions of the protrusions.

8. The acetabular cup assembly kit according to claim 5, wherein the polyethylene bearing has a plurality of second recesses along the outer circumference thereof, the plurality of the second recesses being positioned at upper portions of the protrusions.

* * * * *